United States Patent
Ishida et al.

(10) Patent No.: US 11,744,469 B2
(45) Date of Patent: Sep. 5, 2023

(54) THERMAL DIFFUSION COEFFICIENT MEASURING DEVICE, AND DEEP-BODY THERMOMETER, DEEP-BODY TEMPERATURE MEASURING DEVICE, AND DEEP-BODY TEMPERATURE MEASURING METHOD USING SAME

(71) Applicants: NEC CORPORATION, Tokyo (JP); TOHOKU UNIVERSITY, Sendai (JP)

(72) Inventors: Masahiko Ishida, Tokyo (JP); Ryo Iguchi, Miyagi (JP); Yuki Shiomi, Miyagi (JP); Eiji Saitoh, Miyagi (JP); Ryohto Sawada, Tokyo (JP); Akihiro Kirihara, Tokyo (JP); Koichi Terashima, Tokyo (JP); Yasuyuki Oikawa, Miyagi (JP)

(73) Assignees: NEC CORPORATION, Tokyo (JP); TOHOKU UNIVERSITY, Sendai (JP)

( * ) Notice: Subject to any disclaimer, the term of this patent is extended or adjusted under 35 U.S.C. 154(b) by 1007 days.

(21) Appl. No.: 16/498,838

(22) PCT Filed: Mar. 20, 2018

(86) PCT No.: PCT/JP2018/011118
§ 371 (c)(1),
(2) Date: Sep. 27, 2019

(87) PCT Pub. No.: WO2018/180800
PCT Pub. Date: Oct. 4, 2018

(65) Prior Publication Data
US 2020/0037884 A1    Feb. 6, 2020

(30) Foreign Application Priority Data
Mar. 31, 2017    (JP) .................. 2017-069801

(51) Int. Cl.
*A61B 5/01*    (2006.01)
*G01K 7/02*    (2021.01)
(Continued)

(52) U.S. Cl.
CPC .................. *A61B 5/01* (2013.01); *G01K 7/02* (2013.01); *G01K 13/20* (2021.01); *G06K 19/045* (2013.01);
(Continued)

(58) Field of Classification Search
USPC .............................................. 374/44, 45, 29
See application file for complete search history.

(56) References Cited

U.S. PATENT DOCUMENTS

2002/0150143 A1    10/2002    Tokita et al.
2002/0191675 A1    12/2002    Tokita et al.
(Continued)

FOREIGN PATENT DOCUMENTS

JP    2002-372464 A    12/2002
JP    2003-75262 A    3/2003
(Continued)

OTHER PUBLICATIONS

Translation of JP2003-75262A (Year: 2003).*
(Continued)

*Primary Examiner* — Mirellys Jagan
(74) *Attorney, Agent, or Firm* — Sughrue Mion, PLLC

(57) ABSTRACT

In order to enable the measurement of thermal property information about a subject, this thermal diffusion coefficient measuring device, which is used by contacting the surface of a living body, is provided with: a biological information sensor comprising a temperature sensor and a heat flux sensor; and a heating/cooling control means. The temperature sensor is provided at a position contacting the surface of the living body, and operates so as to detect skin (Continued)

temperature. The heat flux sensor is provided at a position contacting the surface of the living body, while being adjacent to the temperature sensor, and operates so as to detect heat flux on the surface of the living body. The heating/cooling control means enables the measurement of the temperature diffusion coefficient of a thermal resistance component that is present between the biological information sensor and a deep inner portion of the living body.

16 Claims, 12 Drawing Sheets

(51) Int. Cl.
    *G06K 19/04*     (2006.01)
    *G01K 13/20*     (2021.01)
    *A61B 5/00*     (2006.01)

(52) U.S. Cl.
    CPC ........... *A61B 5/0008* (2013.01); *A61B 5/6801* (2013.01); *A61B 2560/04* (2013.01); *A61B 2560/0412* (2013.01); *A61B 2562/0271* (2013.01)

(56) References Cited

U.S. PATENT DOCUMENTS

| | | |
|---|---|---|
| 2010/0121217 A1 | 5/2010 | Padiy et al. |
| 2011/0249701 A1 | 10/2011 | Bieberich et al. |
| 2012/0024833 A1 | 2/2012 | Klewer et al. |
| 2012/0114013 A1 | 5/2012 | Tsuchida |
| 2012/0238901 A1 | 9/2012 | Augustine |
| 2012/0289855 A1 | 11/2012 | Bieberich et al. |
| 2013/0010828 A1 | 1/2013 | Bieberich et al. |
| 2016/0313193 A1 | 10/2016 | Nakagawa et al. |

FOREIGN PATENT DOCUMENTS

| | | | |
|---|---|---|---|
| JP | 2012-98259 A | 5/2012 | |
| JP | 2012-523003 A | 9/2012 | |
| JP | 2013-527434 A | 6/2013 | |
| JP | 2013-170907 A | 9/2013 | |
| JP | 2014-513310 A | 5/2014 | |
| JP | 2015-114291 A | 6/2015 | |
| JP | 5807483 B2 | 9/2015 | |
| JP | 2016-80394 A | 5/2016 | |
| WO | WO-2009107009 A2 * | 9/2009 | ............... G01K 1/16 |
| WO | 2011/126543 A1 | 10/2011 | |
| WO | WO-2018167765 A1 * | 9/2018 | ............... A61B 5/01 |
| WO | WO-2020180454 A9 * | 11/2020 | ........... A61B 5/0008 |

OTHER PUBLICATIONS

Translation of JP2016-80394A (Year: 2016).*
Translation of JP2013-170907A (Year: 2013).*
Kun Koyama, et al., "Ultra-Thin Flexible RFID", [on line], [searched on Mar. 26, 2017], Internet <URL:https://www.jstage.jst.go.jp/article/ejisso/22a/0/22a_0_165/_pdf, 2 pages.
Control of Thermal Conductivity and Thermal Diffusivity and Method of Measurement and Evaluation, published by Science & Technology Co., Ltd., ISBN978-4-903413-60-0, 28 pages.
International Search Report for PCT/JP2018/011118 dated Jun. 12, 2018 [PCT/ISA/210].
Written Opinion for PCT/JP2018/011118 dated Jun. 12, 2018 [PCT/ISA/237].
Office Action dated Jun. 15, 2022 issued by the Japanese Patent Office in Japanese Application No. 2019-509610.

* cited by examiner

THERMAL DIFFUSION COEFFICIENT MEASURING DEVICE, AND DEEP-BODY THERMOMETER, DEEP-BODY TEMPERATURE MEASURING DEVICE, AND DEEP-BODY TEMPERATURE MEASURING METHOD USING SAME

CROSS REFERENCE TO RELATED APPLICATIONS

This application is a National Stage of International Application No. PCT/JP2018/011118, filed on Mar. 20, 2018, which claims priority from Japanese Patent Application No. 2017-069801, filed on Mar. 31, 2017, the contents of all of which are incorporated herein by reference in their entirety.

TECHNICAL FIELD

This invention relates to a thermal diffusion coefficient measuring device and, more particularly, to a deep-body thermometer using the thermal diffusion coefficient measuring device, a deep-body temperature measuring device, and a deep-body temperature measuring method.

BACKGROUND ART

As well known, human deep-body temperature is always stable in the vicinity of 37° C. Herein, temperature of a body surface is called "skin temperature" while temperature of the inside of a body, such as rectal temperature or esophageal temperature is called "deep-body temperature." That is, the "deep-body temperature" indicates temperature of the interior of the body of a human being and is one of vital signs as basic information related to life. For example, the deep-body temperature is used as a barometer of states of blood flow, an autonomic nerve, internal organs, and the like. Therefore, in a medical field and so on, measurement of the deep-body temperature is important in order to monitor the states of the body.

Presently, two techniques as described in the following are used in measurement of the deep-body temperature. The two techniques are (i) a measuring technique using a zero flux method, and (ii) a measuring technique using a heat conduction equation in order to estimate the deep-body temperature from time-series changes in information of temperature and heat flow.

First, description will proceed to (i) the measuring technique using the zero flux method.

This measuring technique is described in, for example, Patent Literature 1. Patent Literature 1 discloses a "zero-heat-flux deep tissue temperature measurement system."

The zero-heat-flux deep tissue temperature measurement system disclosed in Patent Literature 1 measures internal temperature (deep temperature) by way of a probe (patch) having a heater and thermal sensors which are arranged in a zero-heat-flux structure. The probe includes flexible substrate layers and a layer of thermally insulating material. In the measuring technique using the zero-flux method, a part of a body surface is covered with the probe (patch) and the heater is controlled to create a state where heat transfer is compensated in the body surface. Thus, this technique forms a region having temperature extremely close to the deep temperature in the body surface directly under the patch and measures the temperature thereof.

Next, description will proceed to (ii) the measuring technique using the heat conduction equation.

This measuring technique is disclosed in, for example, Patent Literature 2. Patent Literature 2 discloses an "electronic clinical thermometer."

The electronic clinical thermometer disclosed in Patent Literature 2 includes a probe (a sensor head) comprising a heat flux sensor and a temperature sensor. The measuring technique using the heat conduction equation is a technique comprising the steps of bringing the probe (the sensor head) into contact with a body surface; and estimating deep temperature on the basis of respective temporal changes of measured heat fluxes and temperatures. Although Patent Literature 2 never discloses a specific configuration of the heat flux sensor but describes that a working-type thermopile of a laminated structure or a plane development type or the like is used as the heat flux sensor.

In Patent Literature 2, the heat flux sensor and the temperature sensor are disposed adjacent to each other with a space left from each other.

Patent Literature 3 discloses an "internal temperature sensor" including a heat flux sensor using a thermopile. The heat flux sensor disclosed in Patent Literature 3 is arranged on a surface of a substrate and is fabricated through a MEMS (Micro Electro Mechanical Systems) process. The heat flux sensor includes a first temperature measurement part, a second temperature measurement part, and a thin film part which includes the thermopile configured to detect a temperature difference between the first temperature measurement part and the second temperature measurement part. The thin film part is supported by a thermally conductive member, which is configured to conduct, to the second temperature measurement part, heat traveling from a measurement object through the substrate, so as to form a space between the first temperature measurement part and the substrate and to extend in parallel to the substrate.

In Patent Literature 3 also, the heat flux sensor and the temperature sensor are disposed adjacent to each other with a space left from each other.

Patent Literature 4 discloses a "temperature measurement device" which non-locally measures a temperature in the inside of an object. The temperature measurement device disclosed in Patent Literature 4 can estimate the temperature in the inside of a measurement object (a magnetic body layer or a carrier such as a substrate) by utilizing the spin Seebeck effect. The temperature measurement device uses a spin Seebeck element for generating a thermoelectromotive force based on a temperature gradient. The spin Seebeck element includes an electrode film that exhibits a spin-orbit interaction, and a magnetic body layer. A pair of terminals are provided at both ends of the electrode film. The temperature measurement device concurrently uses, as needed, a local thermometer for measuring a local absolute temperature, in addition to the spin Seebeck element. A temperature calculating portion is connected to the pair of terminals and the local thermometer.

The temperature calculating portion includes an electromotive force detection portion, a temperature distribution estimation portion, and a calibration information storing portion. A temperature detection portion detects a voltage between the pair of terminals to generate voltage information indicative of a detected value. The calibration information storing portion preliminarily stores a correspondence relationship between the voltage detected values (and, as needed, a detected value of the local temperature detected by the local thermometer) and a temperature distribution of the object (the magnetic body layer) in a format such as a function or a table. When the voltage between the pair of terminals (and, as needed, the detected temperature detected by the local thermometer) is detected, the temperature distribution estimation portion generates and outputs, on the basis the correspondence relationship stored in the calibration information storing portion, information related to a temperature distribution of the inside (in a thickness direction) of the measurement object (the magnetic body layer or the carrier).

In Patent Literature 4, a temperature distribution model is supposed by carrying out advance or prior calibration in a measurement system using a known heat source, deriving a thermoelectromotive force generation coefficient, and assuming the measurement object having a simple shape (an infinite plane shape or an infinite cylindrical shape).

Furthermore, Non Patent Literature 1 discloses an "Ultra-thin Flexible RFID." The ultra-thin flexible RFID disclosed in Non Patent Literature 1 is a flexible RFID which uses a thin film transistor technique and a flexible technique.

CITATION LIST

Patent Literature

PTL 1: JP 2014-513310 A
PTL 2: JP 2002-372464 A
PTL 3: JP 2015-114291 A
PTL 4: JP 5807483 B

Non Patent Literature

NPL 1: Jun Aoyama, Yoshinari Yamashita, "Ultra-thin Flexible RFID", [on line], [searched on Mar. 26, 2017], Internet <URL:https://www.jstagejstgo.jp/article/ejisso/22a/0/22a_0_1.65/_pdf>
NPL 2: "Control of Thermal Conductivity & Thermal Diffusivity, and Method of Measurement and Evaluation", edited by Science & Technology Co., Ltd. ISBN978-4-903413-60-0

SUMMARY OF INVENTION

Technical Problem

However, the above-mentioned prior art literatures have problems which will be described in the following.

The probe (the patch) disclosed in Patent Literature 1 requires a structure in which the layer of thermally insulating material is sandwiched between the two temperature sensors, so that the device is difficult to be miniaturized or slimmed down. Inasmuch as power consumption in the heater is not little, the probe (sensor head) is generally used in a state where it is always connected to an external power source via a cable. In order to continuously operate an independent device, for example, for about 24 hours, it is necessary to use a very large battery of about 10 Ah. It is therefore difficult to achieve a size which does not interfere with everyday life.

On the other hand, the electronic clinical thermometer disclosed in Patent Literature 2 requires neither a structure in which an insulating layer is sandwiched between two temperature sensors nor the heater and, therefore, achieves the device which need not be connected to a device body with a cable. However, there is a problem in accuracy of the measured value.

The temperature measurement device disclosed in Patent Literature 4 estimates, on the basis of the electromotive force induced in the electrode film of the spin Seebeck element, the temperature distribution of the inside of the measurement object to which the electrode film is mounted. However, in Patent Literature 4, the measurement object is the magnetic body layer or the carrier such as the substrate, and a living body is not supposed.

Specifically, in order to estimate the deep temperature of the living body by measurement in a thermal nonequilibrium state, that is, a state where a heat flow exists in a sensor head portion, not only the temperature at the body surface (the skin temperature) and the measured value of the heat flux but also information of a thickness and a thermal conductivity of a component, which exists in a route from the sensor via the body surface to an internal deep part and possibly serves as thermal resistance, is required.

In a case of application to a human body as the living body, there exist thermal resistance components, which will presently be described, and respective fluctuating factors.

(1) Body surface: errors at an interface, including unevenness of skin, sebum, sweating, body hair, and so on;
(2) Directly under the body surface: errors in thicknesses of epidermis and dermis depending on a position of the body, and individual differences thereof; and
(3) Subcutaneous tissue: errors in a subcutaneous fat amount, a muscle amount, density of blood vessels and so on, depending on the position of the body, and individual differences thereof.

Upon estimating the deep temperature, general values of the respective thermal resistance components are used. This causes a problem that the respective fluctuating factors are eventually reflected as error fluctuations of the value of the deep-body temperature.

For instance, the errors in the body surface in (1) reflect changes in a contact state of the sensor and therefore significantly impair accuracy of information of time-series changes in the deep-body temperature, The errors related to the internal tissue of the human being in (2) and (3) become factors for calculating the deep temperature that substantially reflect differences in measuring positions and the individual differences. This results in difficulties in comparison between data measured under different conditions and statistical treatment thereof.

That is, (ii) the measuring technique using the heat conduction equation is advantageous in that it is possible to achieve miniaturization of the sensor apparatus, low power consumption, and the sensor without being accompanied with the cable for power supply and that it is possible to perform measurement in a short time.

On the other hand, however, the measuring technique is disadvantageous in that intended use is limited because of a problem in the most important point of view, i.e., the accuracy of the measured value.

As a method of measuring a thermal resistance component of a material which is positioned at the outside of the sensor, for example, a $2\omega$ method, a $3\omega$ method, a thereto-reflectance method, and so on are known (see Non Patent Literature 2). These methods are intended to precisely measure periodic application of Joule heat to a metal film vapor-deposited on a surface of the material and a change in response of the surface temperature. Thus, application to the living body is not realistic and, therefore, is not realized.

It is an object of this invention to provide a thermal diffusion coefficient measuring device for measuring thermophysical property information about an object, which is required for more accurate measurement of deep-body temperature in a thermal nonequilibrium state.

In Patent Literature 2 and Patent Literature 3, the temperature sensor and the heat flux sensor are disposed with a space left from each other, it is therefore difficult to accurately estimate the deep temperature. This is because each of Patent Literature 2 and Patent Literature 3 estimates the deep temperature assuming, in a measurement principle thereof, that both a position at which the temperature sensor measures the temperature and a position at which the heat flux sensor measures the heat flow have the same temperature. Furthermore, in Patent Literature 3, it is assumed, as the measurement principle thereof, that the internal temperature sensor is in a thermal equilibrium state and it is therefore impossible to estimate the deep temperature under nonequilibrium.

It is an object of this invention to provide a thermal diffusion coefficient measuring device as well as a deep-body thermometer using same, a deep-body temperature measuring device using same, and a deep-body temperature measuring method using same, which are capable of resolving any of the above-mentioned problems.

Solution to Problem

A thermal diffusion coefficient measuring device according to an example embodiment of the present invention comprises a biological information sensor which comprises an extremely thin temperature sensor for measuring skin temperature and a similarly extremely thin heat flux sensor for measuring heat flux generated in a normal direction to a skin surface; and further comprises a heating/cooling control means which enables measurement of a temperature diffusion coefficient of a thermal resistance component that is present in a route from the biological information sensor to an internal deep part of a living body.

Advantageous Effect of Invention

According to this invention, by having the biological information sensor with the heating/cooling control means in combination, it is possible to measure thermophysical properties of the skin surface or the internal body, which become a significant error factor in an existing measuring technique using the heat conduction equation. By estimating the deep-body temperature using measured values thereof, it is possible to resolve the problem of the errors.

DESCRIPTION OF EMBODIMENTS

Now, description will proceed to an example embodiment of the present invention.

Figure 1:
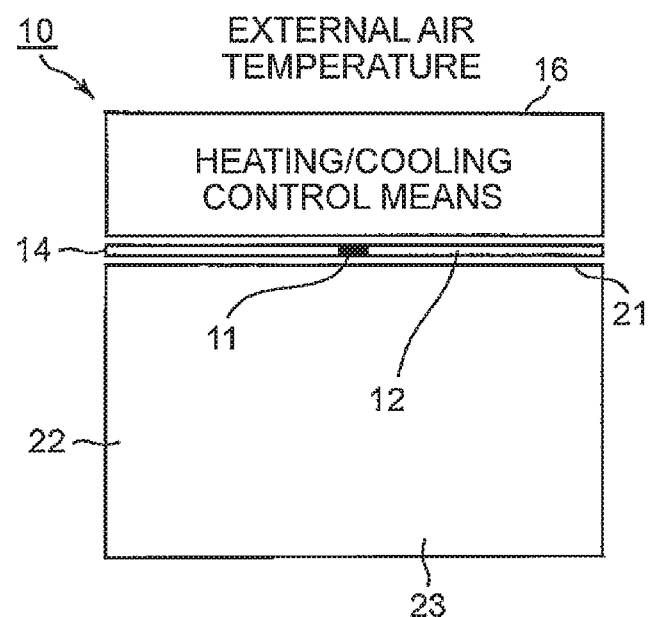
FIG. 1 is a sectional view for illustrating a schematic configuration of a thermal diffusion coefficient measuring device according to an example embodiment of the present invention.

Referring to FIG. 1, a thermal diffusion coefficient measuring device 10 according to an example embodiment of the present invention includes a biological information sensor 14 which comprises an extremely thin temperature sensor 11 for measuring skin temperature and a similarly extremely thin heat flux sensor 12 for measuring heat flux generated in a normal direction to a skin surface 21. Accordingly, the biological information sensor 14 is configured to be flexible. The thermal diffusion coefficient measuring device 10 further includes a heating/cooling control means 16 which enables measurement of a temperature diffusion coefficient of a thermal resistance component that is present in a route from the biological information sensor 14 to a deep part of an internal body 22.

The heating/cooling control means 16 exists so as to cover the temperature sensor 11 and the heat flux sensor 12. The heating/cooling control means 16 includes means for cooling the skin surface 21 in addition to means for heating the skin surface 21.

The heating/cooling control means 16 further includes a mechanism for changing heating and cooling in a certain period and a mechanism for modulating the period.

Next, operation of the thermal diffusion coefficient measuring device 10 will be qualitatively expressed.

Figure 2:
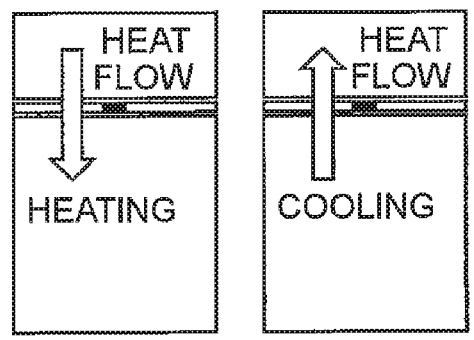
FIG. 2 is a sectional view for illustrating states of a heat flow on heating or cooling using a heating/cooling control means used in the thermal diffusion coefficient measuring device illustrated in FIG. 1.

As shown in FIG. 2, upon heating or cooling using the heating/cooling control means 16. The heat flux sensor 12 provides information of an input amount of the heat flow which flows from the skin surface 21 to the internal body 22 while the temperature sensor 11 provides information of specific heat, density, and thermal conductivity of the internal body 22 on the basis of temperature change obtained as a response to heat input.

Figure 3:
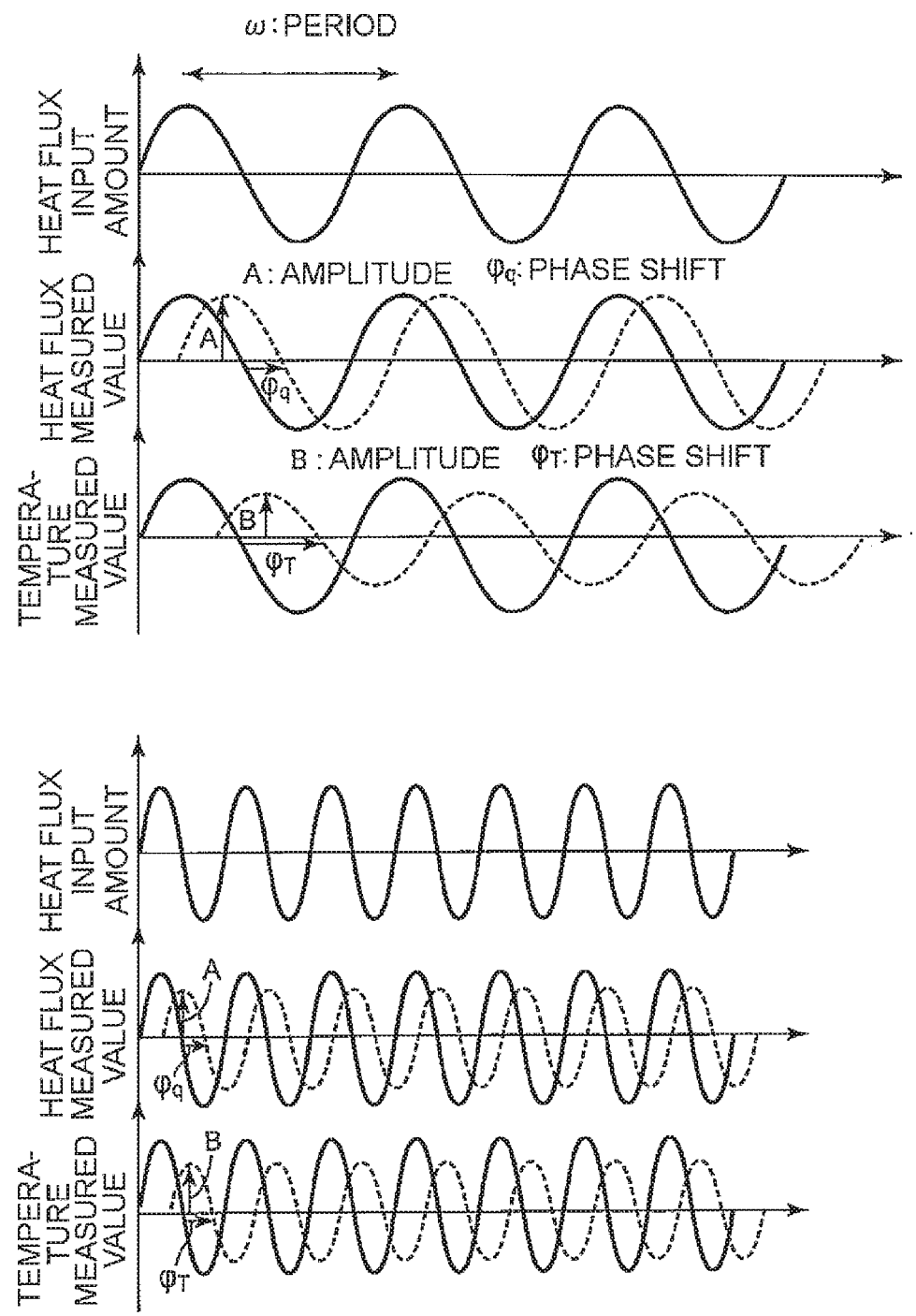
FIG. 3 includes waveform charts for illustrating states of variations in heat flux measured values and temperature measured values when a heating/cooling period w of the heating/cooling control means used in the thermal diffusion coefficient measuring device illustrated in FIG. 1 is changed.

As shown in FIG. 3, by changing a heating/cooling period ω of the heating/cooling control means 16, it is possible to change an effective depth to which a wave of the temperature change permeates from the skin surface 21 into the internal body 22. In this event, by measuring time-series changes of the temperature and the heat flow, it is possible to acquire thermophysical properly information in accordance with the depth.

The thermal diffusion coefficient measuring device 10 can measure information required for estimation of a deep-body temperature 23 by combining those components.

It is noted that the temperature sensor 11 and the heat flux sensor 12 which are used in this case are required to be reduced in heat resistance to the extreme.

Specifically, the heat flux sensor described in Patent Literature 2 or 3 typically has a heat resistance as large as $10^{-3}$ [Km²/W] and is difficult to realize.

In comparison therewith, in the example embodiment, it is possible to reduce the heat resistance by −5 orders of magnitude by using, as the heat flux sensor 12, a thin thermoelectric converter element utilizing the magnetic thermoelectric effect such as the spin Seebeck effect or the anomalous Nernst effect.

Figure 17:
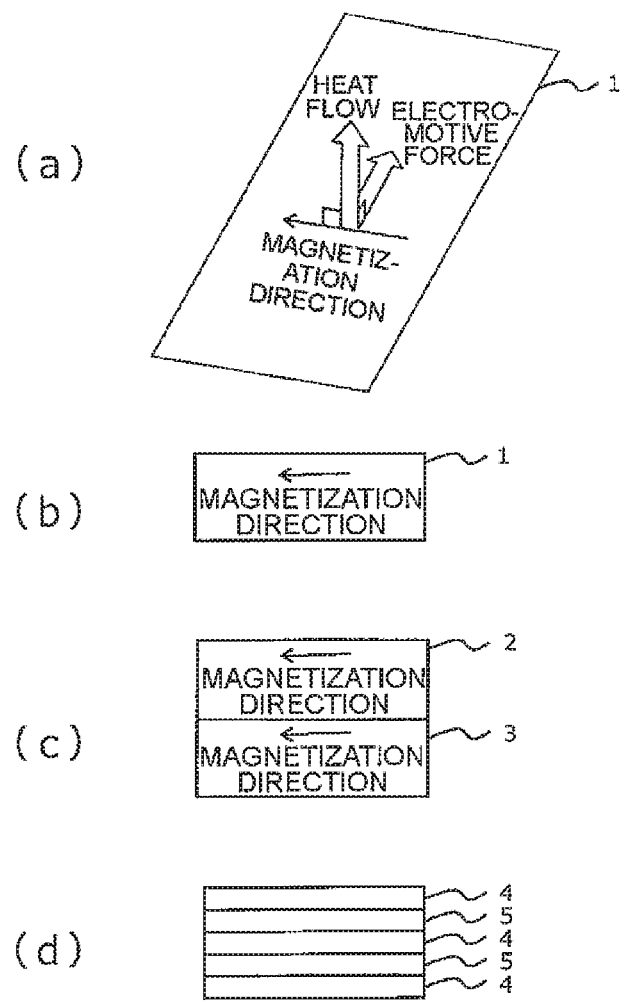
FIG. 17 includes views for illustrating one example of a heat flux sensor used in the example embodiment.

Subsequently, the thin thermoelectric converter element of the example embodiment will be described in detail with reference to FIG. 17.

The heat flux sensor 12 of the example embodiment is a flat thermoelectric converter member which obtains electric power based on thermoelectromotive force generated by temperature difference. FIG. 17(a) is a perspective view for illustrating an outline of the thermoelectric converter member 1. In addition, FIG. 17(b) is an outline of a sectional view of the thermoelectric converter member 1.

The thermoelectric converter member 1 is made of a uniform material which has magnetism, such as ferromagnetism, ferrimagnetism, or antiferromagnetism, and electric conductivity. The thermoelectric converter member 1 has a flat structure. The thermoelectric converter member 1 is made of, for example, a magnetic transition metal having electrons in a 3d orbital, such as Mn, Fe, Co or Ni, or a magnetic metal alloy containing at least one of these transition metals. In addition, the thermoelectric converter member 1 has magnetization or a magnetic moment component which is oriented in parallel to an in-plane direction of the flat structure.

In the thermoelectric converter member 1, a heat flow is generated so as to penetrate the flat structure in a direction perpendicular to a plane thereof. When the thermoelectric converter 1 is put into a state where temperature difference steadily occurs between a surface and a back surface of the flat plane thereof, thermoelectromotive force caused by the anomalous Nernst effect is generated in the thermoelectric converter member 1 in a direction parallel to a direction perpendicular to both of a heat flow direction and a magnetization direction.

The thermoelectromotive force caused by the anomalous Nernst effect has a property such that a sign thereof changes in dependence on a material constituting the thermoelectric converter member 1.

Next, description will proceed to an example where the heat flux sensor 12 comprises a thermoelectric converter member using a compound material. FIG. 17(c) is a sectional view illustrating a configuration of the heat flux sensor 12 using the compound material.

The heat flux sensor 12 comprises an insulating thermoelectric converter material 2 and a conductive thermoelectric converter material 3.

The insulating thermoelectric converter material 2 may be formed using, for example, yttrium iron garnet (YIG: $Y_3Fe_5O_{12}$). The insulating thermoelectric converter material 2 may be made using bismuth(Bi)-doped YIG (Bi:YIG) or ytterbium-doped YIG (YbY$_2$Fe$_5$O$_{12}$). The insulating thermoelectric converter material 2 may be made using a spinel ferrite material comprising a composition MFe$_2$O$_4$ (M is a metallic element and includes any of Ni, Zn, and Co). A material obtained by element substitution on magnetite (Fe$_3$O$_4$) or any other oxide magnetic substance having a garnet structure or a spinel structure may have week electric conductivity. Such an oxide magnetic substance material having the week electric conductivity may also be used as the insulating thermoelectric converter material 2.

The conductive thermoelectric converter material 3 may be formed using a conductor exhibiting the inverse spin Hall effect (a spin orbit interaction). The conductive thermoelectric converter material 3 is formed of, for example, a metal having a relatively large spin orbit interaction, such as Au, Pt, Pd, Ni, Fe, and Bi, any other transition metal having a d orbital or an f orbital, or an alloy material including any of these transition metals. The conductive thermoelectric converter material 3 may also be formed using a metal film material comprising a general metal film material, such as Cu, doped with a material such as Fe or Ir by about 0.5 to 10 mol percent to exhibit a similar effect.

When W, Ta, Mo, Cr, V, or Ti among transition metals is used, it is possible to obtain a voltage of an inverse sign against Au, Pt, Pd, or alloys containing these metals. That is, when W, Ta, Mo, Cr, V, or Ti is used, a direction of an electric current generated due to the inverse spin Hall effect becomes inverted as compared with Au, Pt, Pd, or the alloys containing these metals. In addition, the conductive thermoelectric converter material 3 may be formed using an oxide conductor such as indium tin oxide (ITO) or a magnetic oxide semiconductor having a composition such as CuMo$_2$ or SrMO$_3$ (M is a metal element and includes any of Mn, Ni, Co, and Fe).

The insulating thermoelectric converter material 2 and the conductive thermoelectric converter material 3 are connected to each other via a clean interface. Accordingly, a combination of the insulating thermoelectric converter material 2 and the conductive thermoelectric converter material 3 serves as a spin Seebeck element. If the conductive thermoelectric converter material 3 has magnetism, the combination serves as a compound-type magnetic thermoelectric effect element having the anomalous Nernst effect also.

A thermoelectric converter member of a further multilayered structure may be used as the heat flux sensor 12. FIG. 17(d) is a sectional view for illustrating an example of a configuration of the heat flux sensor 12 having a multilayer structure. The heat flux sensor 12 comprises layers of a first thermoelectric converter material 4 and layers of a second thermoelectric converter material 5 alternately laminated. As the first thermoelectric converter material 4, a material similar to the insulating thermoelectric converter material 2 may be used. As the second thermoelectric converter material 5, a material similar to the conductive thermoelectric converter material 3 may be used.

The heat flux sensor 12 in FIG. 17(d) is configured so that both surfaces thereof are the first thermoelectric converter material 4 and that the layers of the first thermoelectric converter material 4 and the layers of the second thermoelectric converter material 5 are alternately laminated. A combination of the second thermoelectric converter material 5 and the two first thermoelectric converter materials 4 sandwiching the second thermoelectric converter material 5 serves as a spin Seebeck element. Accordingly, the heat flux sensor 12 has a configuration in which a plurality of spin Seebeck elements are laminated. FIG. 17(d) illustrates the configuration in which two spin Seebeck elements are laminated by using three layers of the first thermoelectric converter material 4 and two layers of the second thermoelectric converter material 5. In addition, respective layers of each of the first thermoelectric converter material 4 and the second thermoelectric converter material 5 may be formed of materials different in composition from each other.

Turning back to FIG. 1, the example embodiment realizes acquisition of thermophysical property information of a living body by using the heating/cooling control means 16 which can periodically carry out heating and cooling in addition to the temperature sensor 11 and the heat flux sensor 12.

The heating/cooling control means 16 can be used as needed and may be removed and installed. That is, it is possible to remove the heating/cooling control means 16 while the heating/cooling control means 16 is not used and to again install the heating/cooling control means 16 if necessary.

Description will proceed to effects of this example embodiment.

According to this example embodiment, by having the biological information sensor 14 with the heating/cooling control means 16 in combination, it is possible to measure thermophysical properties of the skin surface 21 and the internal body 22, which become a significant error factor in an existing measuring technique using the heat conduction equation.

By estimating the deep-body temperature 23 using those measured values, it is possible to resolve the problem of the errors.

Now, description will proceed to examples of the present invention.

Example 1

Figure 4:
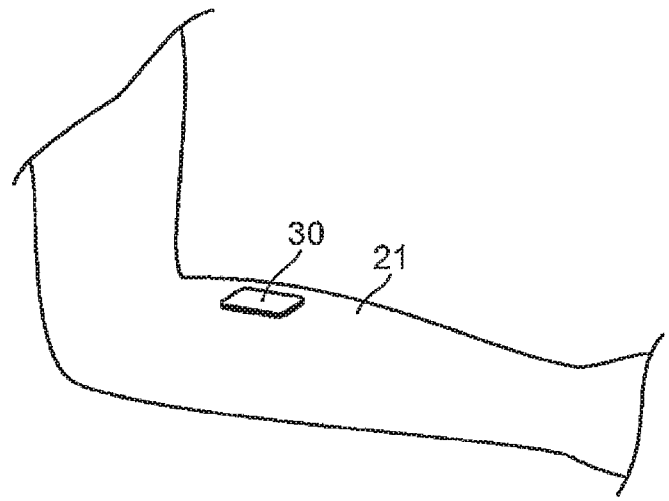
FIG. 4 is a view for illustrating an example in which a deep-body thermometer according to a first example of the present invention is adhered to a skin surface of an arm of a human body.
Figure 5:
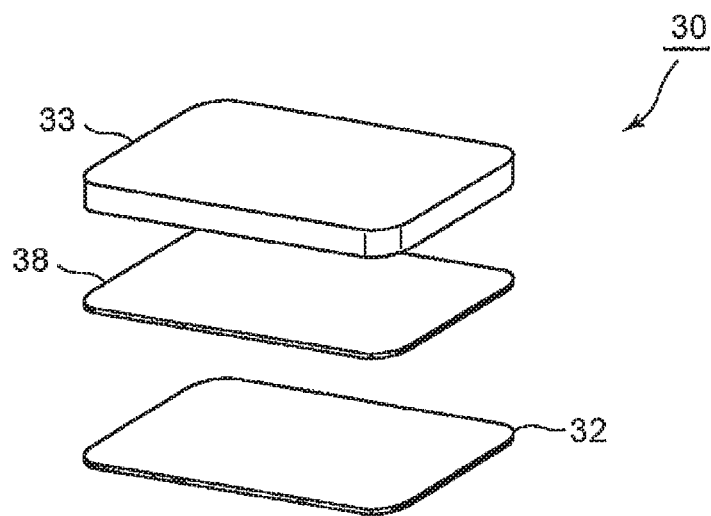
FIG. 5 is an exploded perspective view of the deep-body thermometer illustrated in FIG. 4.
Figure 6:
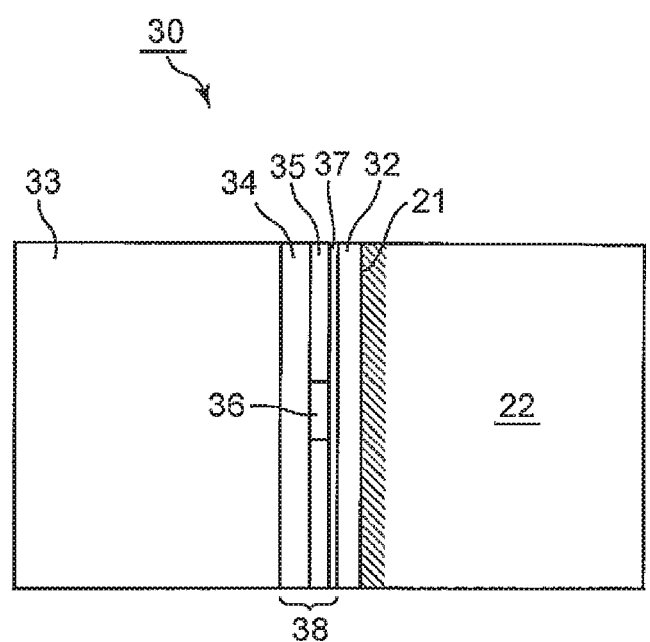
FIG. 6 is a sectional view of the deep-body thermometer illustrated in FIG. 4.

Referring to FIGS. 4 to 6, a deep-body thermometer 30 according to a first example of the present invention will be described in detail.

In the drawings referred to in the following, scales and the numbers in each structure are different from an actual structure in order to facilitate understanding of each structure.

Herein, as shown in FIG. 4, description will proceed to a case where the deep-body thermometer 30 of the first example is used in contact with the skin surface 21 of the living body. FIG. 4 shows an example in which the deep-body thermometer 30 is adhered to the skin surface 21 of an arm of a human body.

FIG. 5 is an exploded perspective view of the deep-body thermometer 30. FIG. 6 is a schematic view as seen from a section of the deep-body thermometer 30.

Now, a configuration of the deep-body thermometer 30 will be described using FIGS. 5 and 6.

As shown in FIG. 5, the deep-body thermometer 30 of the first example mainly comprises three components. A first component is a heat conductive adhesive portion 32 for fixing a deep-body thermometer main part (which will later be described) to the skin surface 21 (see FIG. 4). A second component is a heat flow generating portion 33 for use in generating a heat flow for the purpose of measuring a thermal diffusion coefficient in a route from the skin surface 21 to a deep part of the internal body 22. A third component is the deep-body thermometer main part 38.

As shown in FIG. 6, the deep-body thermometer main part 38 includes a base material film 34, a heat flux sensor 35, a temperature sensor 36, and a protection film 37.

The heat flow generating portion 33 serves as the above-mentioned heating/cooling control means 16. The deep-body thermometer main part 38 serves as the above-mentioned biological information sensor. Accordingly, the deep-body thermometer 30 also serves as the above-mentioned thermal diffusion coefficient measuring device.

The heat conductive adhesive portion 32 may be made of a material which includes, as a main material, an acrylic-based adhesive, a rubber-based adhesive, or a silicone-based adhesive and, as a filler material, carbon or high heat conduction ceramics added thereto in order to improve thermal conductivity.

As the heat flow generating portion 33, a commercially-available Peltier element comprising a BiTe-based semiconductor material or a spin Peltier element comprising a laminated film including a magnetic insulator and a metal may be used.

The base material film 34 may comprise a polyvinyl chloride-based, a polyurethane-based, or a polyolefin-based polymer film used in a first-aid adhesive tape and so on. For the purpose of enhancing intensity, the base material film 34 may comprise, partially or entirely, a material including a material such as polyether, polyethylene, or polyimide.

As the heat flux sensor 35, an ultra-thin heat flux sensor using the spin Seebeck effect or the anomalous Nernst effect is used. Details of the heat flux sensor 35 will later be described.

The temperature sensor 36 may be formed using a thermocouple or a thin-film resistance thermometer which is generally used.

The protection film 37 is manufactured using a material similar to that of the base material film 34 for the purpose of insulating various sensor parts and preventing mechanical breakage thereof.

(Measurement Principle of Thermal Diffusion Coefficient)

Figure 7:
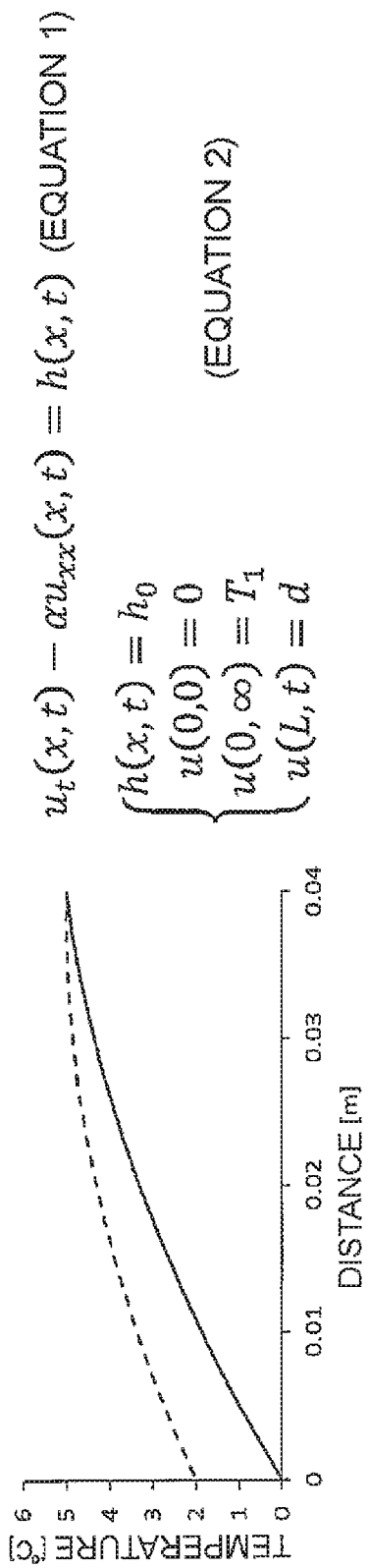
FIG. 7 includes views for use in describing a method of calculating, by using the deep-body thermometer illustrated in FIGS. 4 to 6, thermal diffusion coefficient $\alpha$, which is related to thermal conductivity $\lambda$, specific heat density $c_p$, and density $\rho$, and the thermal conductivity $\lambda$.
Figure 7:
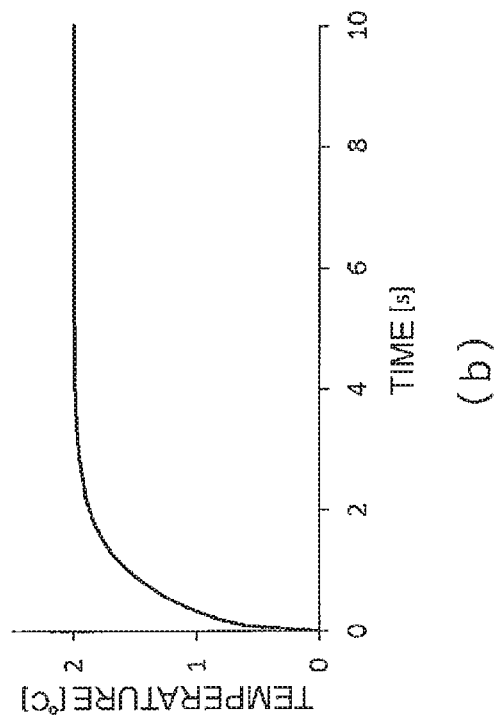

Referring to FIG. 7, description will proceed to a method of calculating, using the deep-body thermometer (the thermal diffusion coefficient measuring device) 30, the thermal diffusion coefficient $\alpha$ which is related to thermal conductivity $\lambda$, specific heat density $c_p$ and density p, as well as the thermal conductivity $\lambda$.

It is considered that the thermal diffusion coefficient measuring device 30 and temperature of the internal body 22 as a measured object can be expressed with a one-dimensional thermal diffusion model. It is assumed that a direction from the skin surface 21 toward the internal body 22 is positive, a position defined by a value between 0 and L is x, and a positive time interval is t. Then, a temperature distribution u(x, t) of a system can be described in a form of a diffusion-type partial differential equation shown in Equation 1 of FIG. 7.

Herein, $u_t$ means a result obtained by first-order differentiation of the temperature distribution u with respect to the time interval t, and $u_{xx}$ means a result obtained by second-order differentiation of the temperature distribution u with respect to the position x. In addition, a coefficient $\alpha = \lambda/(\rho c_p)$ is the thermal diffusion coefficient, and the right-hand side of Equation 1 is a function h which corresponds to a distribution of a heat generation amount in the internal body 22.

In solving this Equation 1, a condition shown in Equation 2 of FIG. 7(*a*) is assumed in order to simply explain the measurement principle. First, it is considered that, as an initial condition, the heat generation amount h is equal to a constant $h_0$ uniform throughout the entirety of the internal body 22 and a temperature scale is such that an initial temperature u(0, 0) at the skin surface 21 is equal to 0, that is, the skin surface temperature is used as a reference value. In addition, it is assumed that a temperature of a position L corresponding to the deep-body temperature 23 is equal to d. In addition, the skin surface temperature at a time instant ∞ is assumed to be u(0, ∞)=$T_1$. Then, Equation 1 of FIG. 7(*a*) is solved.

An analytical solution of this thermal diffusion equation can be expressed as a sum of a term of a series representing transient changes and other steady-state terms, as the following Math. 1.

$$u(x, t) = -\frac{h_0}{2\alpha}x^2 + \left(\frac{h_0 L}{2\alpha} + \frac{d - T_1}{L}\right)x + \quad [\text{Math. 1}]$$

$$T_1 - \frac{4T_1}{\pi^2}\sum_{n=1}^{\infty}\frac{1}{n^2}e^{-\alpha(\frac{n\pi}{L})^2 t}\cos\frac{n\pi x}{L}$$

It is understood that, at a limit of t=∞, the total sum of the series is zero and a temperature profile represented by a quadratic curve is obtained. Assuming that the thermal diffusion coefficient α=0.2 mm/s, a heat generation density of a human body is 0.8 W/m², the skin surface temperature $T_1$=0° C., the deep-body temperature d=5° C. and the distance L=4 cm, a graph which is convex upward is obtained as depicted by a solid line in FIG. 7(*a*).

Next, description will proceed to evaluation of the thermal diffusion coefficient α. There are several means as a measurement method.

For instance, upon measurement, the deep-body thermometer 30 is adhered to the skin surface 21 on the presumption that the deep-body temperature d, the skin surface temperature $T_1$, and a temperature of the deep-body thermometer main part 38 before use, namely, room temperature $T_R$ are different from one another. In this event, the temperature of the skin surface 21 changes to a new temperature $T_1$ which establishes a new thermal equilibrium state because the deep-body thermometer 30 has predominant thermal resistance.

On the basis of the above-mentioned analytical solution, a temperature change in the new thermal equilibrium state in a case of $T_1$=2° C. is depicted by a dotted line in FIG. 7(*a*) and a transient change of the temperature at a body surface x=0 is shown in FIG. 7(*b*). Inasmuch as a change rate of the transient change depends on the thermal diffusion coefficient α as is apparent from Equation, it is possible to calculate α by performing simple calculation on the measured temperature change.

Alternatively, it is possible to measure the thermal diffusion coefficient α based on the temperature change in a case where a constant heat flow amount is supplied from the heat flow generating portion 33.

Under certain circumstances, it is possible to calculate a more accurate value of thermal diffusion coefficient α by combining several measurement methods.

Subsequently, in order to calculate the thermal conductivity, a time-dependent boundary condition is given in which a time-dependent periodic temperature change u(0, t)=$q_0$ sin ωt occurs at the skin surface 21.

This periodic temperature change is generated using a function of the heat flow generating portion 33 provided in the thermal diffusion coefficient measuring device 30. Strictly, it is possible to perform a heat transfer analysis in a state where the heat flow generating portion 33 is included. Herein, for simplification, an analytical approach is applied for an area of x≥0 with $h_0$=0 assuming that the heat generation $h_0$ does not affect a transient change.

Figure 8:
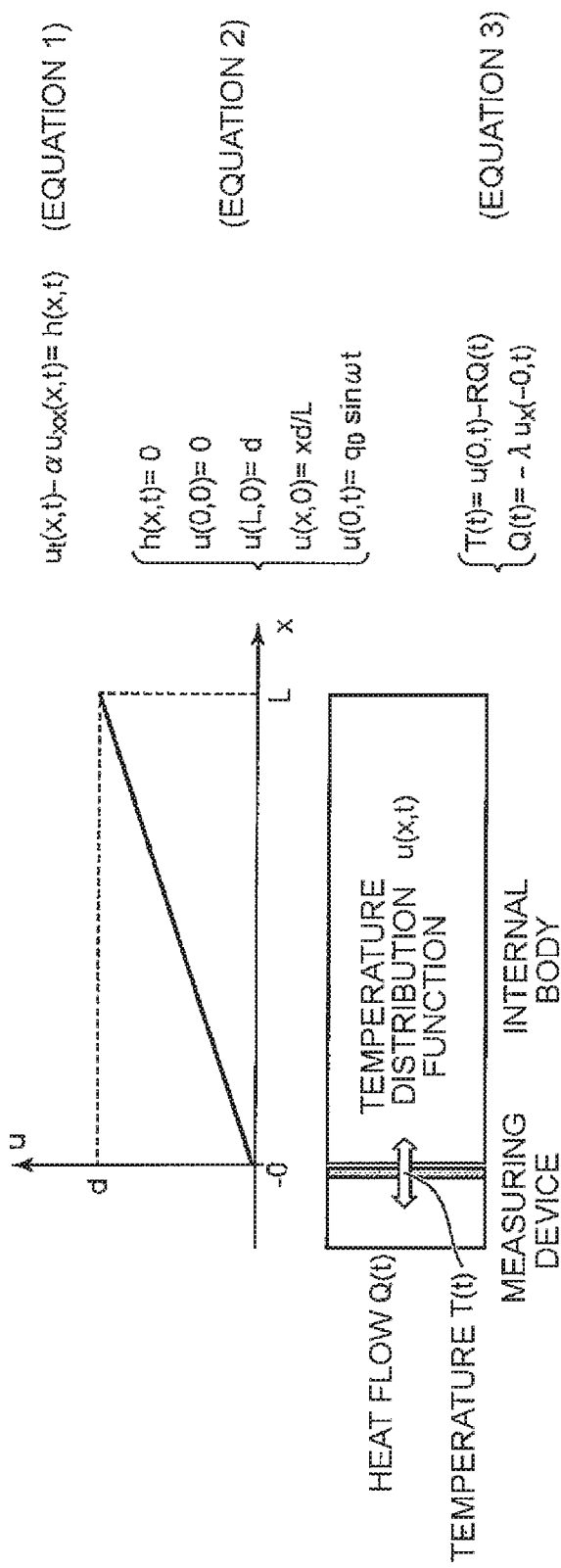
FIG. 8 includes views for use in describing that temperature T (t) and heat flux density Q (t), which are measured values of the temperature sensor and the heat flux sensor provided in the thermal diffusion coefficient measuring device, can be expressed using u(x, t) and thermal resistance R that is present in the skin surface.

The temperature T(t) and the heat flux density Q(t), which are measured values of the temperature sensor 36 and the heat flux sensor 35 provided in the thermal diffusion coefficient measuring device 30, can be expressed using u(x, t) and the heat resistance R which exists in the skin surface 21, as shown in Equation 3 of FIG. 8.

The analytical solution of u(x, t) can be expressed in a form of the following Math. 2.

$$u(x, t) = \quad [\text{Math. 2}]$$
$$q_0 \sin\omega t + \frac{x}{L}(d - q_0 \sin\omega t) + \sum_{n=1}^{\infty}\sin\frac{n\pi x}{L}\int_0^t B_n(s)e^{-\alpha(\frac{n\pi}{L})^2(t-s)}ds$$

$$B_n(s) = \frac{2}{L}\int_0^L \left(h_0 + q_0\omega\left(1 - \frac{x}{L}\right)\cos\omega s\right)\sin\frac{n\pi x}{L}dx$$

In actual measurement, an amplitude intensity $Q_R$ of a component synchronized with u(0, t)=$q_0$ sin ωt is first extracted from a signal Q(t). This is similar to a synchronous signal component measured using a lock-in amplifier or the like.

It is understood that Q(t) can be calculated by differentiating the analytical solution of u(x, t) with respect to the position x and defining x=0 and that, when a coefficient of sinωt therein is extracted, the coefficient can be expressed by the following Math. 3.

$$Q_R = d\lambda/L - \lambda/2 + 2\lambda q_0 c_0 \sqrt{(2\omega/\alpha)} \quad [\text{Math. 3}]$$

Herein, $c_0$ is a constant which can be analytically calculated. That is, $Q_R$ has a nature of increasing in linear proportion to $\sqrt{\omega}$. Accordingly, by measuring the intensity of $Q_R$ with two or more different values of ω and by plotting the intensity with respect to $\sqrt{\omega}$, it is possible to calculate the thermal conductivity λ based on the intercept at ω=0 and a slope thereof.

Furthermore, it is also possible to measure a contact resistance R based on the measured values of T(t) and Q(t).

(Measurement Principle of Deep-Body Temperature)

The deep-body temperature 23 can be estimated using the thermal conductivity λ preliminarily measured and the analysis equation which is calculated in the foregoing.

Once the thermal conductivity λ is calculated in the above-mentioned manner (i.e. after the calibration is carried out once), it is possible to estimate the deep-body temperature 23 on the basis of the heat flux (the thermoelectromotive force) measured by the heat flux sensor 35 and the skin temperature detected by the temperature sensor 36. In other words, after the calibration is carried out once, the heat flow generating portion 33 is no longer necessary and only the deep-body thermometer main part 38 and the heat conductive adhesive portion 32 are required.

Therefore, the heat flow generating portion (the heating/cooling control means) 33 is provided to be installable and removable to and from the deep-body thermometer main part (the biological information sensor) 38.

As mentioned above, the thermal diffusion coefficient α and the thermal conductivity λ are related to each other.

Figure 9:
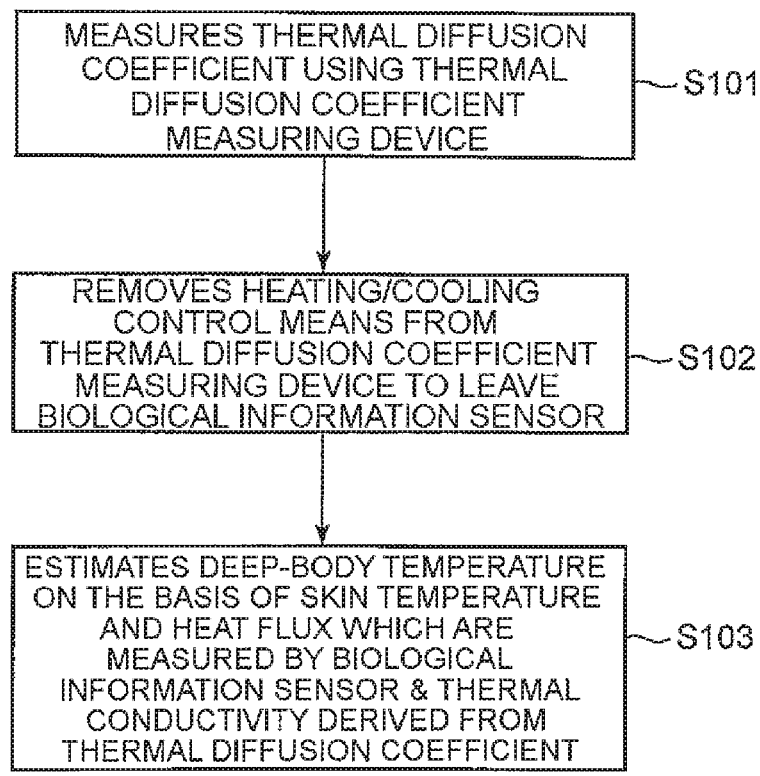
FIG. 9 is a flow chart for use in describing a deep-body temperature measuring method according an example of the present invention.

Accordingly, as illustrated in FIG. 9, the deep-body temperature measuring method according to this example includes three steps: a measuring step; a removing step; and an estimating step. In the measuring step, the thermal diffusion coefficient is measured using the deep-body thermometer (the thermal diffusion coefficient measuring device) 30 (step S101). In the removing step, the heat flow generating portion (the heating/cooling control means) 33 is removed from the deep-body thermometer (the thermal diffusion coefficient measuring device) 30 to leave the deep-body thermometer main part (the biological information sensor) 38 (step S102). In the estimating step, the deep-body temperature is estimated on the basis of the skin temperature and the heat flux which are measured by the deep-body thermometer main part (the biological information sensor) 38 and the thermal conductivity derived from the above-mentioned thermal diffusion coefficient (step S103). Each of the measuring step, the removing step, and the estimating step may be repeatedly carried out as needed. As a result, it is possible to improve accuracy of the measurement and to prevent the degradation of accuracy due to changing conditions.

Next, description will proceed to an effect of the first example.

By having the heat flow generating portion (the heating/cooling control means) 33 in combination, the first example exhibits an effect that the thermophysical properties of the skin surface and the internal body 22, which become a significant error factor in the existing measuring technique using the heat conduction equation, can be measured. It is possible to resolve the problem of the errors by estimating the deep-body temperature 23 using the measured value.

Example 2

Figure 10:
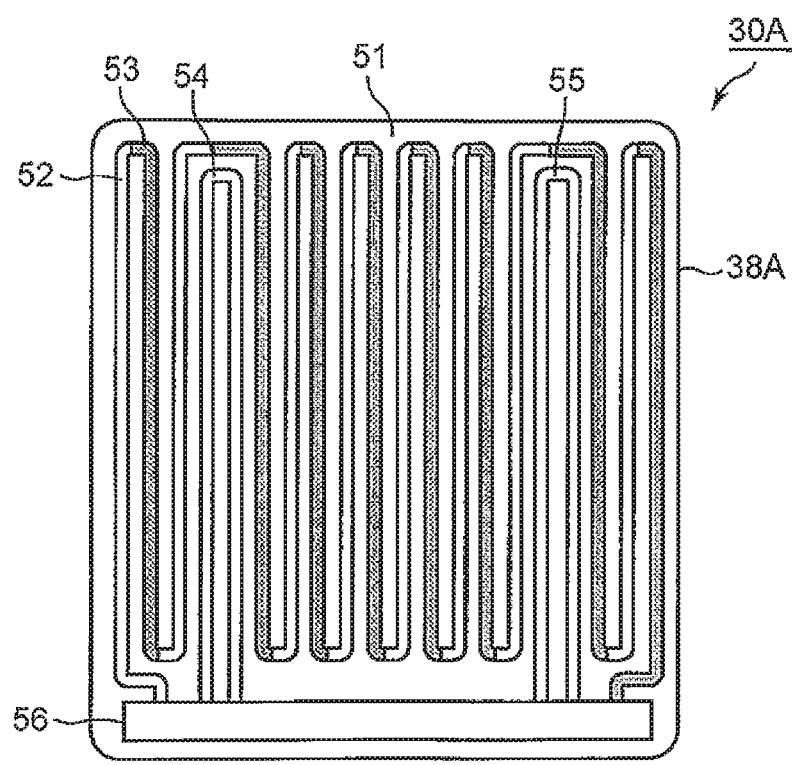
FIG. 10 is a schematic view for illustrating a configuration of a deep-body thermometer main part used in a deep-body thermometer according a second example of the present invention.
Figure 11:
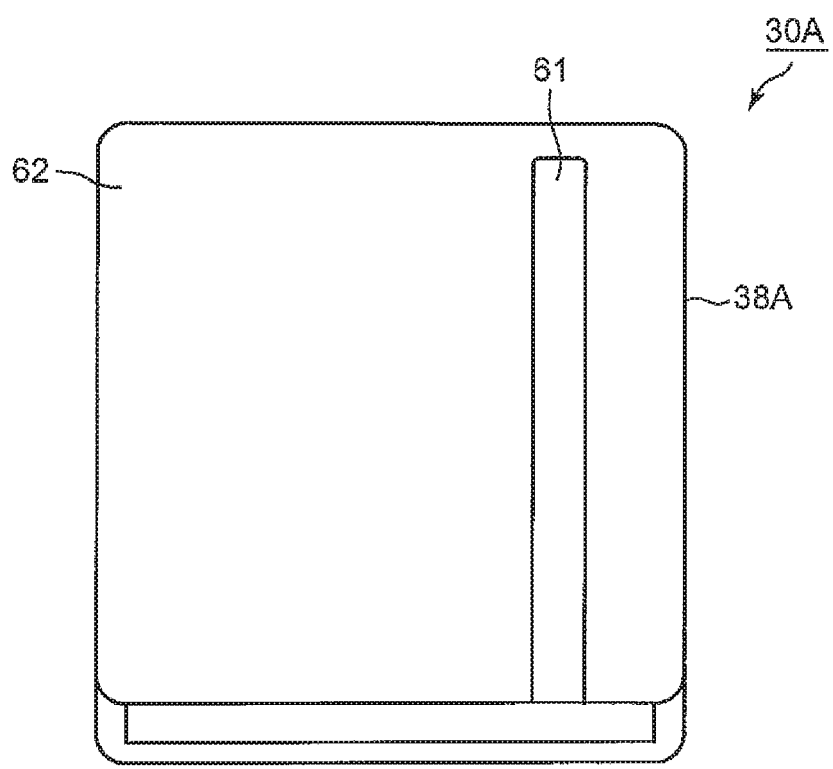
FIG. 11 is a plan view for illustrating external appearance of the deep-body thermometer main part illustrated in FIG. 10.

Referring to FIGS. 10 and 11, a deep-body thermometer 30A according to a second example of the present invention will be described in detail.

The first example necessitates the use in a state where room temperature is stabilized because it is assumed that outside temperature is stationary.

However, in general life, there are a lot of factors giving a change in a heat equilibrium state, such as a change in clothing, a change in external air temperature, and so on. It is therefore desirable to use a configuration based on the supposition that these factors exert influence upon the measured values.

For instance, the deep-body temperature is not an index having a nature of widely changing in a short time interval and therefore it is not difficult to exclude a transient change in an external factor. On the other hand, for instance, when the external air temperature or the like changes in synchronism with a change occurring over a period of several ten minutes to several hours in association with sleep or a circadian rhythm, it is difficult to separate these changes.

The most effective method of excluding such errors is to use two or more pairs of heat flux sensors and temperature sensors, which have different heat transfer paths.

Using FIGS. 10 and 11, description will proceed to a configuration of a deep-body thermometer main part 38A used in the deep-body thermometer 30A according to the second example. FIG. 10 is a view for schematically representing an in-plane configuration of various sensors with the base material film 34 (FIG. 6) of the first example disposed as a substrate 51.

As the substrate 51 corresponding to the base material film 34, a polyimide film having a thickness of 10 microns is used. On a surface of the substrate 51, a folded electrode type heat flux sensor comprising first thermoelectric material thin films 52 and second thermoelectric material thin films 53, a first resistance thermometer 54, and a second resistance thermometer 55 are manufactured by means of stencil mask vapor deposition.

Accordingly, a combination of the first thermoelectric material thin films 52 and the second thermoelectric material thin films 53 constitutes the heat flux sensor 12 shown in FIG. 1. A combination of the first resistance thermometer 54 and the second resistance thermometer 55 serves as the temperature sensor 11 shown in FIG. 1.

Herein, as the first thermoelectric material thin films 52, thin films each having a thickness of 30 nm formed of platinum-iron alloy having a composition ratio of 1:1 and, as the second thermoelectric thin films 53, pure iron thin films each having a thickness of 30 nm were manufactured by means of sputtering vapor deposition using a stencil mask.

Furthermore, each of the first resistance thermometer 54 and the second resistance thermometer 55 was manufactured from a platinum film having a thickness of 10 nm.

Subsequently, a controller 56 was adhered and mounted so as to secure good electrical contact with each of the first thermoelectric material thin films 52, the second thermoelectric material thin films 53, the first resistance thermometer 54, and the second resistance thermometer 55.

Furthermore, as shown in FIG. 11, thin film patterns constructing respective sensors are protected by means of a protection film 61 disposed so as to cover a whole of the second resistance thermometer 55 and a protection film 62 disposed so as to cover the heat flux sensor (52, 53) of the deep-body thermometer 30A and a whole of the first and the second resistance thermometers 54 and 55.

Next, description will proceed to an effect of the second example.

In addition to the effect of the first example mentioned above, the second example has an effect that the errors due to the factors giving a change in the thermal equilibrium state can be eliminated. This is because two or more pairs of the heat flux sensors 52, 53 and the temperature sensors 54, 55, which have different heat transfer paths, are used.

Example 3

Figure 12:
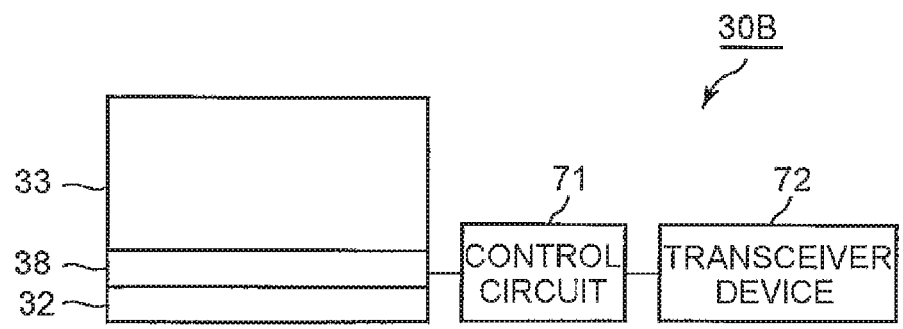
FIG. 12 is a view for illustrating a deep-body thermometer according a third example of the present invention.

Referring to FIG. 12, description will proceed to a deep-body thermometer 30B according to a third example of this invention.

The illustrated deep-body thermometer 30B is similar in structure and operation to the deep-body thermometer 30 according to the first example illustrated in FIGS. 4 to 6 except that a control circuit 71 and a transceiver device 72 are further provided.

The illustrated deep-body thermometer 30B can communicate with an outside wirelessly by comprising the control circuit 71 and the transceiver device 72. An operation mode of the control circuit 71 can be set from the outside wirelessly.

Accordingly, a combination of the control circuit 71 and the transceiver device 72 serves as a transmitting means (71, 72) for transmitting, as sensed data, the skin temperature detected by the temperature sensor 36 (FIG. 6) and the heat flux (the output voltage) detected by the heat flux sensor 35 (FIG. 6) to the outside.

In addition, the transmitting means (71, 72) is configured to transmit, at least once, the temperature diffusion coefficient measured by using the heat flow generating portion 33, before the heat flow generating portion 33 serving as the heating/cooling control means is removed from the biological information sensor 38.

Figure 13:
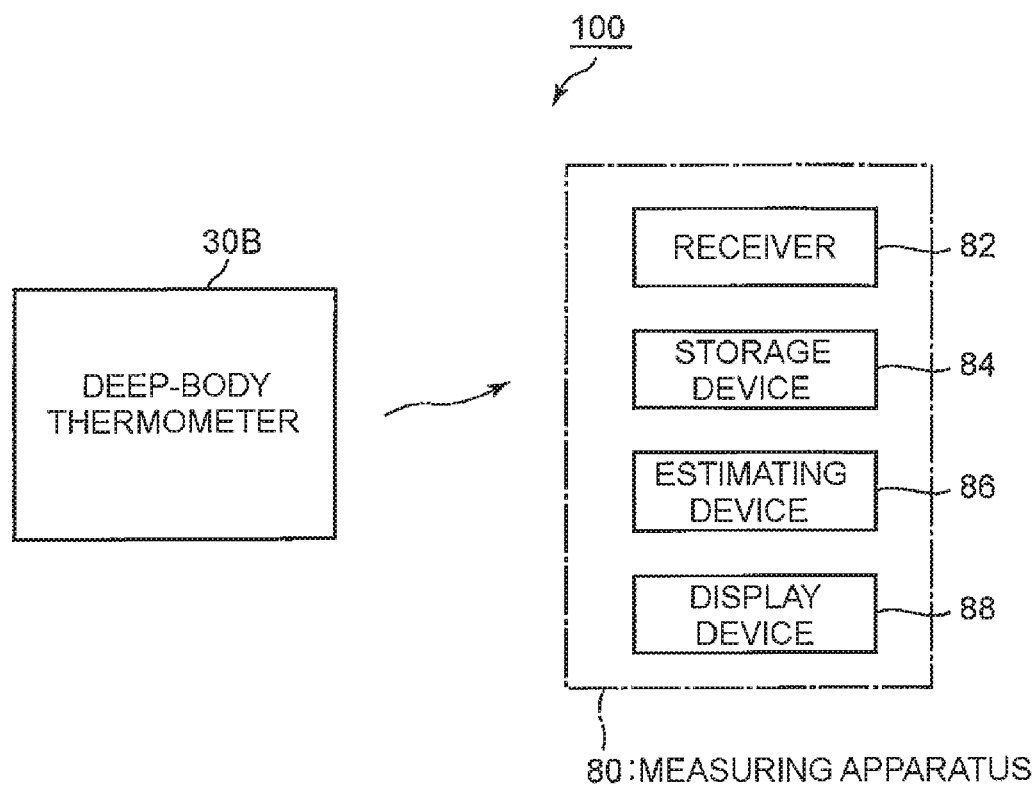
FIG. 13 is a block diagram for illustrating a deep-body temperature measuring device including the deep-body thermometer illustrated in FIG. 12.

Furthermore, the transceiver device 72 comprises a transceiver portion configured to carry out wireless communication using a Radio Frequency Identification (RFID) system. As the RFID system, an ultra-thin flexible RFID described in the above-mentioned Non Patent Literature 1 may be used, FIG. 13 is a block diagram for illustrating a configuration of a deep-body temperature measuring device 100 including the deep-body thermometer 30B.

The deep-body temperature measuring device 100 further includes a measuring apparatus 80 in addition to the deep-body thermometer 30B.

The measuring apparatus 80 includes a receiver 82, a storage device 84, an estimating device 86, and a display device 88.

The receiver 82 receives the above-mentioned sensed data and the above-mentioned thermal diffusion coefficient which are transmitted from the deep-body thermometer (the thermal diffusion coefficient measuring device) 30B. The storage device 84 memorizes the received thermal diffusion coefficient therein.

The estimating device 86 estimates the deep-body temperature on the basis of the received sensed data and the thermal conductivity derived from the memorized thermal diffusion coefficient. The display device 88 displays the estimated deep-body temperature.

In addition to the above-mentioned effect of the first example, the third example also exhibits an effect that the sensed data and the like and the thermal diffusion coefficient can be transmitted to the outside wirelessly.

Example 4

Figure 14:
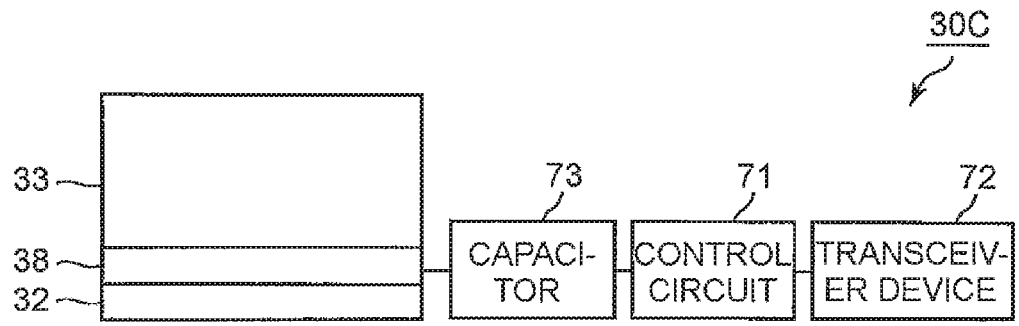
FIG. 14 is a view for illustrating a deep-body thermometer according a fourth example of the present invention.

Referring to FIG. 14, description will proceed to a deep-body thermometer 30C according to a fourth example of this invention.

The illustrated deep-body thermometer 30C is similar in structure and operation to the deep-body thermometer 30B according to the third example illustrated in FIG. 12 except that a capacitor 73 is further provided.

The thermoelectromotive force is always generated from the heat flow sensor 35 (FIG. 6). As such, the deep-body thermometer 30C according to the fourth example boosts the generated thermoelectromotive force for accumulation in the capacitor 73.

In addition to the effect of the first example mentioned above, the fourth example also exhibits an effect that it is possible to drive itself independently without an external battery or power supply from the outside and to transmit the sensed data and the thermal diffusion coefficient to the outside wirelessly.

Example 5

Figure 15:
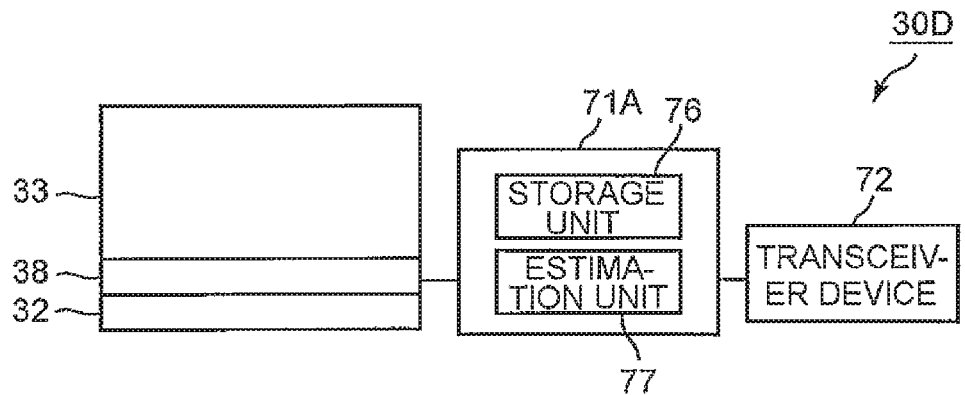
FIG. 15 is a view for illustrating a deep-body thermometer according a fifth example of the present invention.

Referring to FIG. 15, description will proceed to a deep-body thermometer 30D according to a fifth example of this invention.

The illustrated deep-body thermometer 30D is similar in structure and operation to the deep-body thermometer 30B according to the third example illustrated in FIG. 12 except that a controller 71A is used in place of the control circuit 71.

The controller 71A includes a storage unit 76 and an estimation unit 77. The controller 71A may be implemented by, for example, an IC (integrated circuit) chip which serves as a microprocessor or a microcontroller.

The storage unit 76 memorizes the thermal diffusion coefficient therein. The estimation unit 77 estimates, on the basis of the skin temperature detected by the temperature sensor 36 (FIG. 6) and the heat flux (the output voltage) detected by the heat flux sensor 35 (FIG. 6), the deep-body temperature of an interior of the living body in accordance with the thermal conductivity derived from the thermal diffusion coefficient memorized in the storage unit 76.

The transceiver device 72 transmits, as measured data, the estimated deep-body temperature to the outside.

Figure 16:
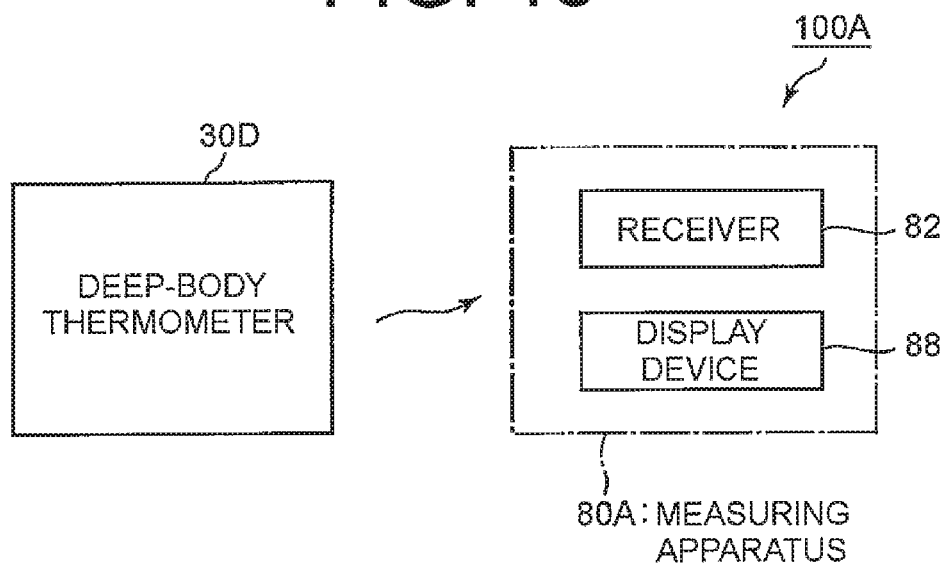
FIG. 16 is a block diagram for illustrating a deep-body temperature measuring device including the deep-body thermometer illustrated in FIG. 15.

FIG. 16 is a block diagram for illustrating a configuration of a deep-body temperature measuring device 100A including the deep-body thermometer 30D.

The deep-body temperature measuring device 100A includes a measuring apparatus 80A in addition to the deep-body thermometer 30D.

The measuring apparatus 80A includes the receiver 82 and the display device 88.

The receiver 82 receives the above-mentioned measured data transmitted from the deep-body thermometer 30D.

The display device 88 displays the received measured data as the deep-body temperature of the living body.

In addition to the effect of the first example mentioned above, the fifth example also exhibits an effect that it is possible to transmit, as the measured data, the estimated deep-body temperature to the outside wirelessly.

While the invention has been particularly shown and described with reference to the example embodiment thereof, the invention is not limited to the example embodiment mentioned above. It will be understood by those of ordinary skill in the art that various changes in configuration and details may be made without departing from the spirit and scope of the present invention as defined by the claims.

A whole or a part of the example embodiment and examples described above may be described as, but not limited to, the following supplementary notes.

(Supplementary Note 1)

A thermal diffusion coefficient measuring device to be used in contact with a skin surface of a living body, the thermal diffusion coefficient measuring device comprising:

a biological information sensor which comprises:

a temperature sensor which is provided at a position to contact the skin surface of the living body and which is configured to operate so as to detect skin temperature; and a thin heat flux sensor which is provided at a position to contact the skin surface of the living body while being adjacent to the temperature sensor and which is configured to operate so as to detect heat flux generated in a normal direction to the skin surface of the living body;

wherein the thermal diffusion coefficient measuring device further comprises a heating/cooling control means which enables measurement of a temperature diffusion coefficient of a thermal resistance component that is present in a route from the biological information sensor to an internal deep part of the living body.

(Supplementary Note 2)

The thermal diffusion coefficient measuring device according to Supplementary Note 1, wherein the thin heat flux sensor comprises:

a substrate to be brought into contact with the skin surface of the living body; and a magnetic conductor film provided on the substrate with a certain magnetization direction having a component in parallel to a film surface thereof and formed of a magnetic conductor, wherein the thin heat flux sensor is configured to produce, as a potential difference within the surface of the magnetic conductor film, a temperature gradient perpendicular to the surface of the magnetic conductor film.

(Supplementary Note 3)

The thermal diffusion coefficient measuring device according to Supplementary Note 1, wherein the thin heat flux sensor comprises:

a substrate to be brought into contact with the skin surface of the living body;

a magnetic conductor film provided on the substrate with a certain magnetization direction having a component in parallel to a film surface thereof and formed of a magnetic conductor;

a magnetic insulating film provided in contact with the magnetic conductor film, having a certain magnetization direction including a component parallel to a film surface thereof, and formed of a magnetic insulator; and an electrode provided on the magnetic conductor film with a conductive material exhibiting a spin-orbit interaction;

wherein the thin heat flux sensor is configured to produce, as a potential difference within the surface of the magnetic conductor film, a temperature gradient perpendicular to the surface of the magnetic conductor film.

(Supplementary Note 4)

The thermal diffusion coefficient measuring device according to any one of Supplementary Notes 1 to 3, wherein the biological information sensor is configured to be flexible.

(Supplementary Note 5)

The thermal diffusion coefficient measuring device according to any one of Supplementary Notes 1 to 4, wherein the heating/cooling control means is provided so as to be removable from and installable in the biological information sensor.

(Supplementary Note 6)

The thermal diffusion coefficient measuring device according to Supplementary Note 5, further comprising a transmitting means configured to transmit, as sensed data, the skin temperature detected by the temperature sensor and the heat flux detected by the thin heat flux sensor to the outside, wherein the transmitting means is configured to transmit, at least once, the temperature diffusion coefficient measured by using the heating/cooling control means, before the heating/cooling control means is removed from the biological information sensor.

(Supplementary Note 7)

The thermal diffusion coefficient measuring device according to Supplementary Note 6, wherein the transmitting mean comprises a transmitter configured to carry out wireless communication with a Radio Frequency Identification (RFID) system.

(Supplementary Note 8)

The thermal diffusion coefficient measuring device according to Supplementary Note 6 or 7, further comprising a capacitor configured to accumulate, as electric power, electromotive force of the heat flux detected by the thin heat flux sensor.

(Supplementary Note 9)

A deep-body temperature measuring device comprising the thermal diffusion coefficient measuring device according to any one of Supplementary Notes 6 to 8 and a measuring apparatus, wherein the measuring apparatus comprises:

a receiver configured to receive the sensed data transmitted from the thermal diffusion coefficient measuring device;

an estimating device configured to estimate, on the basis of the received sensed data, deep-body temperature of the living body in accordance with thermal conductivity derived from the thermal diffusion coefficient; and a display device configured to display the estimated deep-body temperature.

(Supplementary Note 10)

The deep-body temperature measuring device according to Supplementary Note 9, wherein the measuring apparatus further comprises a storage device configured to memorize the thermal diffusion coefficient therein, wherein the estimating device is configured to estimate the deep-body temperature on the basis of the received sensed data and the thermal conductivity derived from the memorized thermal diffusion coefficient.

(Supplementary Note 11)

A deep-body thermometer, comprising:

the thermal diffusion coefficient measuring device according to any one of Supplementary Notes 1 to 5; and an estimating means configured to estimate, on the basis of the skin temperature detected by the temperature sensor and the heat flux detected by the thin heat flux sensor, deep-body temperature in an interior of the living body in accordance with a conductivity derived from the thermal diffusion coefficient.

(Supplementary Note 12)

The deep-body thermometer according to Supplementary Note 11, further comprising a memorizing means configured to memorize the thermal diffusion coefficient therein, wherein the estimating means is configured to estimate the deep-body temperature on the basis of the detected skin temperature, the detected heat flux, and the thermal conductivity derived from the memorized thermal diffusion coefficient.

(Supplementary Note 13)

The deep-body thermometer according to Supplementary Note 11, wherein the estimating means is configured to acquire the thermal diffusion coefficient using the heating/cooling control means and to estimate the deep-body temperature on the basis of the detected skin temperature, the detected heat flux, and the thermal conductivity derived from the thermal diffusion coefficient.

(Supplementary Note 14)

The deep-body thermometer according to any one of Supplementary Notes 11 to 13, further comprising a transmitting means configured to transmit, as measured data, the estimated deep-body temperature to the outside.

(Supplementary Note 15)

The deep-body thermometer according to Supplementary Note 14, wherein the transmitting means comprises a transmitter configured to carry out wireless communication using a Radio Frequency Identification (RFID) system.

(Supplementary Note 16)

The deep-body thermometer according to Supplementary Note 14 or 15, further comprising a capacitor configured to accumulate, as electric power, electromotive force of the heat flux detected by the thin heat flux sensor.

(Supplementary Note 17)

A deep-body temperature measuring device comprising the deep-body thermometer according to any one of Supplementary Notes 14 to 16 and a measuring apparatus, wherein the measuring apparatus comprises:
a receiver configured to receive the measured data transmitted from the deep-body thermometer; and
a display device configured to display the received measured data as the deep-body temperature of the living body.
(Supplementary Note 18)
A deep-body temperature measuring method comprising the steps of:
measuring the thermal diffusion coefficient using the thermal diffusion coefficient measuring device according to Supplementary Note 5;
removing the heating/cooling control means from the thermal diffusion coefficient measuring device to leave the biological information sensor; and
estimating deep-body temperature based on skin temperature and heat flux, which are measured by the biological information sensor, and on thermal conductivity derived from the thermal diffusion coefficient.

REFERENCE SIGNS LIST

1: thermoelectric converter member
2: insulating thermoelectric converter material
3: conductive thermoelectric converter material
4: first thermoelectric converter material
5: second thermoelectric converter material
10: thermal diffusion coefficient measuring device
11: temperature sensor
12: heat flux sensor
14: biological information sensor
16: heating/cooling control means
21: skin surface
22: internal body
23: deep-body temperature
30, 30A, 30B, 30C, 30D: deep-body thermometer (thermal diffusion coefficient measuring device)
32: heat conductive adhesive portion
33: heat flow generating portion
34: base material film
35: heat flux sensor
36: temperature sensor
37: protection film
38, 38A: deep-body thermometer main part (biological information sensor)
51: substrate
52: first thermoelectric material thin film
53: second thermoelectric material thin film
54: first resistance thermometer
55: second resistance thermometer
56: controller
61, 62: protection film
71: control circuit
71A: controller
72: transceiver device
73: capacitor
76: storage unit
77: estimation unit
80, 80A: measuring apparatus
82: receiver
84: storage device
86: estimating device
88: display device
100, 100A: deep-body temperature measuring device

The invention claimed is:

1. A thermal diffusion coefficient measuring device to be used in contact with a skin surface of a living body, the thermal diffusion coefficient measuring device comprising:
a biological information sensor which comprises:
a temperature sensor which is provided at a position to contact the skin surface of the living body and which is configured to detect a skin temperature; and
a thin heat flux sensor which is provided at a position to contact the skin surface of the living body while being adjacent to the temperature sensor and which is configured to detect heat flux generated in a normal direction to the skin surface of the living body; and
a heating/cooling control unit which changes heating and cooling the skin surface in a certain period so as to enable measurement, by the biological information sensor, of a thermal diffusion coefficient of a thermal resistance component that is present in a route from the biological information sensor to an internal deep part of the living body,
wherein the heating/cooling control unit is provided so as to be removable from and installable to the biological information sensor,
wherein the thermal diffusion coefficient measuring device further comprises a transmitting unit configured to transmit, as sensed data, the skin temperature detected by the temperature sensor and the heat flux detected by the thin heat flux sensor to the outside, and
wherein the transmitting unit is configured to transmit, at least once, the thermal diffusion coefficient measured by using the heating/cooling control unit before the heating/cooling control unit is removed from the biological information sensor.

2. The thermal diffusion coefficient measuring device as claimed in claim 1,
wherein the thin heat flux sensor comprises:
a substrate to be brought into contact with the skin surface of the living body; and
a magnetic conductor film provided on the substrate with a certain magnetization direction having a component in parallel to a film surface thereof and formed of a magnetic conductor,
wherein the thin heat flux sensor is configured to produce, as a potential difference within the surface of the magnetic conductor film, a temperature gradient perpendicular to the surface of the magnetic conductor film.

3. The thermal diffusion coefficient measuring device as claimed in claim 1,
wherein the thin heat flux sensor comprises:
a substrate to be brought into contact with the skin surface of the living body;
a magnetic conductor film provided on the substrate with a certain magnetization direction having a component in parallel to a film surface thereof and formed of a magnetic conductor;
a magnetic insulating film provided in contact with the magnetic conductor film, the magnetic insulating film having a certain magnetization direction including a component parallel to a film surface thereof, and the magnetic insulating film being formed of a magnetic insulator; and
an electrode provided on the magnetic conductor film with a conductive material exhibiting a spin-orbit interaction;
wherein the thin heat flux sensor is configured to produce, as a potential difference within the surface of the magnetic conductor film, a temperature gradient perpendicular to the surface of the magnetic conductor film.

4. The thermal diffusion coefficient measuring device as claimed in claim 1, wherein the biological information sensor is configured to be flexible.

5. The thermal diffusion coefficient measuring device as claimed in claim 1, wherein the transmitting unit comprises a transmitter configured to carry out wireless communication using a Radio Frequency Identification (RFID) system.

6. The thermal diffusion coefficient measuring device as claimed in claim 1, further comprising a capacitor configured to accumulate, as electric power, electromotive force of the heat flux detected by the thin heat flux sensor.

7. A deep-body temperature measuring device comprising the thermal diffusion coefficient measuring device claimed in claim 1 and a measuring apparatus,
wherein the measuring apparatus comprises:
a receiver configured to receive the sensed data transmitted from the thermal diffusion coefficient measuring device;
an estimating device configured to estimate, on the basis of the received sensed data, a deep-body temperature of the living body in accordance with a thermal conductivity derived from the thermal diffusion coefficient transmitted by the transmitting unit; and
a display device configured to display the estimated deep-body temperature.

8. The deep-body temperature measuring device as claimed in claim 7,
wherein the measuring apparatus further comprises a storage device configured to memorize the thermal diffusion coefficient therein, and
wherein the estimating device is configured to estimate the deep-body temperature on the basis of the received sensed data and the thermal conductivity derived from the memorized thermal diffusion coefficient.

9. A deep-body thermometer, comprising:
the thermal diffusion coefficient measuring device claimed in claim 1; and
an estimating unit configured to estimate, on the basis of the skin temperature detected by the temperature sensor and the heat flux detected by the thin heat flux sensor, a deep-body temperature in an interior of the living body in accordance with a thermal conductivity derived from the thermal diffusion coefficient.

10. The deep-body thermometer as claimed in claim 9, further comprising a memorizing unit configured to memorize the thermal diffusion coefficient therein,
wherein the estimating unit is configured to estimate the deep-body temperature on the basis of the detected skin temperature, the detected heat flux, and the thermal conductivity derived from the memorized thermal diffusion coefficient.

11. The deep-body thermometer as claimed in claim 9,
wherein the estimating unit is configured to acquire the thermal diffusion coefficient using the heating/cooling control unit and to estimate the deep-body temperature on the basis of the detected skin temperature, the detected heat flux, and the thermal conductivity derived from the thermal diffusion coefficient.

12. The deep-body thermometer as claimed in claim 9, further comprising a transmitting unit configured to transmit, as measured data, the estimated deep-body temperature to the outside.

13. The deep-body thermometer as claimed in claim 12, wherein the transmitting unit comprises a transmitter configured to carry out wireless communication using a Radio Frequency Identification (RFID) system.

14. The deep-body thermometer as claimed in claim 12, further comprising a capacitor configured to accumulate, as electric power, electromotive force of the heat flux detected by the thin heat flux sensor.

15. A deep-body temperature measuring device comprising the deep-body thermometer claimed in claim 12 and a measuring apparatus,
wherein the measuring apparatus comprises:
a receiver configured to receive the measured data transmitted from the deep-body thermometer; and
a display device configured to display the received measured data as the deep-body temperature of the living body.

16. A deep-body temperature measuring method comprising:
measuring the thermal diffusion coefficient using the thermal diffusion coefficient measuring device claimed in claim 1;
removing the heating/cooling control unit from the thermal diffusion coefficient measuring device to leave the biological information sensor; and
estimating a deep-body temperature based on the skin temperature and the heat flux, which are measured by the biological information sensor, and on a thermal conductivity derived from the thermal diffusion coefficient.

* * * * *